United States Patent [19]

Niedballa et al.

[11] Patent Number: 5,686,492
[45] Date of Patent: Nov. 11, 1997

[54] DISUBSTITUTED P-FLUOROBENZENESULFONAMIDES

[75] Inventors: Ulrich Niedballa; Johannes Platzek; Bernd Raduchel, all of Berlin, Germany

[73] Assignee: Schering Aktiengesellschaft, Berlin, Germany

[21] Appl. No.: 487,092

[22] Filed: Jun. 6, 1995

[30] Foreign Application Priority Data

Dec. 22, 1994 [DE] Germany .......... 44 47 389.3

[51] Int. Cl.⁶ .......... C07C 317/00; A61K 31/19
[52] U.S. Cl. .......... 514/562; 562/37; 562/43; 562/44; 562/430; 424/9.34; 128/653.4; 514/534; 514/541
[58] Field of Search .......... 562/430, 37, 43, 562/44; 514/562, 534, 541; 424/9.34; 128/653.4

[56] References Cited

U.S. PATENT DOCUMENTS 3,920,444 11/1975 Harrington et al. .......... 562/430
5,130,119 7/1992 Blaszkiewicz et al. .......... 424/9
5,210,290 5/1993 Gries et al. .......... 562/430

FOREIGN PATENT DOCUMENTS 368429 5/1990 European Pat. Off.
447013 9/1991 European Pat. Off.
538469 4/1993 European Pat. Off.

*Primary Examiner*—Johann Richter
*Assistant Examiner*—Laura L. Stockton
*Attorney, Agent, or Firm*—Millen, White, Zelano & Branigan, P.C.

[57] ABSTRACT

Described herein are disubstituted p-fluorobenzenesulfonamides, containing a $CF_3$ group, of general formula I

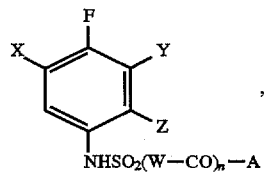

which are suitable as NMR diagnostic agents.

13 Claims, No Drawings

DISUBSTITUTED P-FLUOROBENZENESULFONAMIDES

The invention relates to disubstituted p-fluorobenzenesulfonamides containing a $CF_3$ group, their use as NMR diagnostic agents, diagnostic agents which contain these p-fluorobenzene-sulfonamides, and a process for the production of these compounds and agents.

Modern medical technology makes it possible to visualize extremely small morphological structures at a resolution that comes close to that of tissue sections in anatomy textbooks.

It is not possible, however, even with the aid of ultrasonic diagnosis, diagnostic radiology, nuclear medicine, and nuclear spin tomography, to obtain data on the metabolic-physiological state of a living organism's tissue. For a more exact diagnosis and especially for planning and monitoring of the course of therapeutic intervention, however, this information is of considerable importance since optimum treatment can be successful only if an assessment of its effect is possible early on.

An important parameter for metabolic-physiological activity is pH. Many pathological processes bring about a change of hydrogen ion concentration. One of the best-known examples is the release of lactic acid as a result of inadequate oxygen supply and thus anaerobic metabolism of glucose. Anaerobic glycolysis takes place virtually wherever sufficient oxygen supply is no longer assured.

SUMMARY OF THE INVENTION

Short-term acidification can be detected, for example, in areas of highest muscular activity. Here, however, the lactic acid that accumulates is removed relatively quickly during the resting phase, so that no hyperacidity can be detected in the resting muscle. The situation is different, however, in areas of permanent oxygen debt. In ischemic areas (infarction), a shift in pH occurs because of increased anaerobic glycolysis. Similar effects can be observed in rapidly growing neoplasms. In addition to a disruption of regulation, an oxygen deficiency exists in the area of a tumor, so that acidification also occurs here due to anaerobic metabolism of carbohydrates.

The determination of tissue pH thus provides important information on the function, condition, and growth of the cells, so that, for example, it is desirable to locate metabolic acidoses (Am. J. Physiol. 246, R 409, 1984: R. Nuccitelli, D. W. Deamer, Eds. 1982 Intracellular pH: Its Measurement, Regulation and Utilization in Cellular Functions, Liss. New York).

In addition to measuring pH with pH electrodes, NMR spectroscopy has also been used recently for this purpose. With this method, it was possible for the first time to determine the pH of tissue without external influence.

The determination of pH with the aid of NMR spectroscopy is based on measuring the signals of a chemical compound that is present in a pH-dependent, reversible equilibrium. If this equilibrium is slow relative to the NMR time scale, the signals of all components can be obtained, and the signal intensities will correspond to the concentrations of the equilibrium components. In the case of a quick equilibrium, however, only one signal can be measured, and the chemical shift is provided by the chemical shift of the equilibrium components and their concentration.

In a two-component equilibrium, pH can then be calculated with the aid of the Henderson-Hasselbalch equation if the $pK_a$ value and the chemical shift of the components are known.

The following table shows which atomic nuclei are basically suitable for NMR imaging or spectroscopy:

| Nucleus | Frequency at 1 tesla MHZ | rel. measuring sensitivity $^1H = 1$ | Concentration in biol. tissue | Chemical shift | Possibility of chemical modification | $T_1$-relaxation times |
|---|---|---|---|---|---|---|
| $^1H$ | 42.6 | 1.0 | 100 mol/l | small | very high | 0.1–3 sec |
| $^{19}F$ | 40.1 | 0.8 | <<1 mmol/l | very large | very high | 1–5 sec |
| $^{23}Na$ | 11.3 | 0.09 | 100 mmol/l | — | practically zero | <0.1 sec |
| $^{31}P$ | 17.2 | 0.06 | 10 mmol/l | average | limited | 1–5 sec |
| $^{13}C$ | 10.7 | 0.0002 | 1 mmol/l | very large | very high | 1–10 sec |

For 15 years, the $^{31}P$ nucleus has been used as a noninvasive measuring probe for the measurement of intracellular pH (J. Biol. Chem. 248, 7276, 1973). In this case, the pH-sensitive signal is the signal of inorganic phosphate from the hydrogen phosphate-dihydrogen phosphate equilibrium; the $^{31}P$ signal of phosphocreatine is used as reference.

The use of the $^{31}P$ nucleus for the determination of pH also has its limits, however: thus, an exact determination of the pH in a readily located tissue volume in humans is not possible even when using 2T nuclear spin tomographs. This is due to both the relatively low phosphate concentrations and the fact that the $^{31}P$ signal is difficult to detect in terms of measuring technique. Interfering signals in the area of the inorganic phosphate, superposition of the inorganic P-signal with other P-metabolites, or the absence of a reference signal can prevent pH measurement. Other difficulties lie in the low sensitivity of the nucleus and the low pH-dependence of the chemical shift. The accuracy of the pH measurement is influenced particularly by the determination of the chemical shifts of the signals and is no better than 0.2 pH. In addition, resonance signals may be completely absent when endogenous phosphates are used because the compounds accumulate in only low concentrations (e.g., in the intestines or in Ehrlich ascitic tumor cells), so that determination of pH is not possible.

Because of these conditions, only a quite inaccurate determination of pH in comparatively large volumes is possible. To plot a satisfactory $^{31}P$ spectrum, signals from the measured volume of about 100 ccm are recorded in an accumulation period of 15 minutes.

When nuclei other than $^{31}P$ are used, the $^{19}$fluorine nucleus is the nucleus of choice since it provides an easily measurable NMR signal that is very similar to that of the hydrogen proton (just like $^1H$, it has a nuclear spin of ½), i.e., the same receiver and transmitter coils as in $^1H$-NMR diagnosis can be used, it has a high sensitivity (about 83% of $^1$H), it is present in 100% of the cases, and the signals are distributed over a large frequency range. Other advantages that can be cited include the absence of fluorine in the organism (with the exception of the teeth), so that no complications with endogenous F signals can occur (absence of a $^{19}$F background signal), as well as the advantageous chemical availability.

Data which can be obtained using F molecules in NMR diagnosis cannot be produced by any other diagnostic imaging or quasi-imaging processes: the signal may be greatly changed in the body—depending on the chemical state, and it thus makes it possible to quantify biochemical reactions and to observe physiological processes directly. Despite these advantageous properties, mention must be made of the problematic concentration. A useful experiment requires $^{19}$F concentrations of >1 mmol of F/l, i.e., the compounds to be administered must exhibit excellent compatibility and have good water solubility, so that the smallest possible volumes can be used when solutions of high concentrations are employed.

The frequency (chemical shift) of a fluorine line is determined by the position of the F atom in the molecule. This also holds true in principle for all other atomic nuclei, but the chemical shift is especially pronounced in the case of the fluorine atom. To observe or to quantify a shift of the fluorine signal, a reference line is required. This frequency line can be the $^1$H signal, an external F standard, or an unvarying F line that is also present in the area to be measured. This reference line can itself be present in another, similarly dispersed molecule or preferably in the molecule used as an indicator. The most advantageous situation exists in the last-mentioned case since here only one substance is administered, and no problems whatsoever occur with susceptibility effects, so that unambiguous identification of the signals is possible.

There is therefore a need to find suitable compounds that react to a change in pH with a changed measurement variable (resonance frequency) in the NMR spectrum, with the simultaneous existence of a reference line. Further, these compounds or diagnostic agents that contain these compounds must exhibit the following properties:

a) a large chemical shift per pH unit;

b) suitable pK values for in vivo measurements;

c) pharmacokinetics suitable for diagnosis;

d) a high concentration in the target organs sufficient for measurement;

e) good compatibility and low toxicity;

f) metabolic stability;

g) good chemical stability and shelf life;

h) good water solubility.

The compounds described previously (and only for in vitro studies!) [Annals of the New York Academy of Science, S. M. Cohen, Ed. 1987, 508 33] do not meet these requirements. Thus, e.g., more exact determination of pH with them than with $^{31}$P is not possible since the pH-dependence of the chemical shift is too low ($\leq$1 ppm/pH) and/or their pH values lie outside the physiological range and/or their resonance frequencies are dependent not only on pH, but also on field strength. Also, because of their poor compatibility, the compounds described are not suitable for animal experiments or even clinical use.

The compounds described in European Patent Application No. 0 447 013 fulfill the required physical conditions, such as, e.g., measurement range, sensitivity, solubility, and temperature range very well, but are not yet optimum with respect to their biological properties (e.g., release of histamine).

An object of the invention is thus to make available compounds and agents, which exhibit the above-mentioned properties but without the weaknesses of the previously mentioned compounds, as well as to provide a process for their production. This object is achieved by the invention.

Upon further study of the specification and appended claims, further objects and advantages of this invention will become apparent to those skilled in the art.

It has been found that fluorobenzenesulfonamides of general formula I

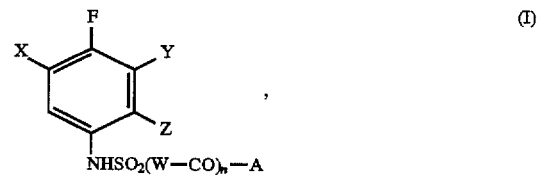

(I)

in which

Z stands for a CF$_3$ group or a hydrogen atom,

Y stands for a C$_1$-C$_6$ alkyl group, which can be substituted by 1 to 4 hydroxy groups or interrupted by 1 to 2 oxygen atoms, or is a (CH$_2$)$_o$COOH or (CH$_2$)$_o$CONR$^1$R$^2$ group with o meaning numbers 0 or 1 and R$^1$ and R$^2$, independently of one another, meaning hydrogen or a C$_1$-C$_6$ alkyl group optionally substituted by 1 to 4 hydroxy groups, X stands for a hydrogen atom or for one of the meanings indicated for Y, W stands for a C$_0$-C$_6$ alkylene group, which can be substituted by 1 to 4 hydroxy groups or interrupted by 1 to 2 oxygen atoms, where C$_0$ is a direct bond, n stands for numbers 0 or 1, A stands for radicals —OH, OR$^3$, —CF$_3$, —CH$_2$CF$_3$, —NH—CR$^3$(CF$_3$)—COOH or —NHCH$_2$ COOH with R$^3$ meaning a hydrogen atom or a straight-chain or branched-chain C$_1$-C$_6$ alkyl group optionally substituted by 1 to 2 hydroxy group(s), provided that X stands for a hydrogen atom if Z means a CF$_3$ group, that X has one of the meanings indicated for Y, if Z stands for a hydrogen atom, and that optionally the acid groups present in the molecule are present in the form of their amides or in the form of salts with organic or inorganic bases, are surprisingly very well suited for the production of especially compatible NMR diagnostic agents.

As alkyl substituents in the definitions of X, Y, R$^1$, R$^2$ and R$^3$, saturated, unsaturated, straight-chain or branched-chain hydrocarbons with up to 6 C atoms, preferably saturated hydrocarbons with up to 4 carbon atoms, are included, for example, which alkyl groups in the case of X, Y, R$^1$ and R$^2$ may optionally be substituted by 1 to 4 hydroxy group(s), in the case of R$^3$ may optionally be substituted by 1 to 2 hydroxy groups, and in the case of X and Y may further optionally be interrupted by 1 to 2 oxygen atom(s).

AS examples for Y, the groups

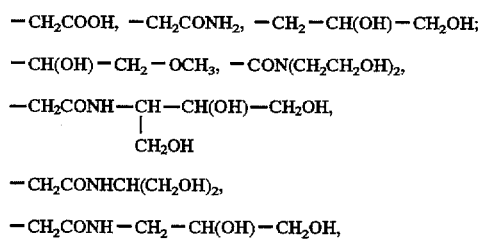

—CH₂CONH—CH₂(CH)₄—CH₂OH
|
OH can be mentioned.

For W, the following groups can be mentioned as examples:

—CH₂—; —CH₂—CH₂—; —CH₂—CH₂—O—CH₂—CH₂—;

—CH₂—CH(OH)—CH₂—; —(CH₂)₃—; —(CH₂)₄—;

—CH₂—CH(COOH)—CH₂—; CH₂—CH₂—O—CH₂—.

As examples for substituents (W—CO)ₙ—A, the groups

—CF₃, —CH₂CF₃, —CH₂COOH, —CH₂CH₂COOH,

—CH₂CONHCH₂COOH, —CH₂CONHC(CF₃)COOH,
|
CH₃

—CH₂CONHCH(CF₃)COOH, can be mentioned.

The acid hydrogen atoms present in the compound of general formula I optionally can be completely or partially replaced by cations of inorganic and/or organic bases or amino acids. Suitable inorganic cations are, for example, the lithium ion, the potassium ion, the calcium ion, the magnesium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acid or neutral amino acids.

The production of the disubstituted p-fluorobenzenesulfonamides of general formula I containing a CF₃ group takes place in that in a way known in the art, compounds of general formula II

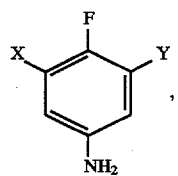     (II)

in which
Y and X have the above-indicated meaning, and the hydroxy and carboxy groups optionally contained in them optionally are present in protected form,
are reacted with compounds of general formula III ClSO₂(W—CO)ₙ—A     (III), in which
W, and n A have the above-indicated meaning, and the hydroxy and carboxy groups optionally contained in A optionally are present in protected form,
then the optionally present protective groups are removed, and if desired, the acid groups optionally present in the molecule are converted with organic or inorganic bases to the corresponding salts or,
optionally after activation of the acid groups, by reaction with an amine to the corresponding amides.

As acid protective groups, lower alkyl, aryl and aralkyl groups, for example the methyl, ethyl, propyl, n-butyl, t-butyl, phenyl, benzyl, diphenylmethyl, triphenylmethyl, bis(p-nitrophenyl)-methyl group, as well as trialkylsilyl groups are suitable.

The acids can also be used in the form of their salts, preferably as ammonium salt.

The cleavage of the acid protective groups takes place according to the processes known to one skilled in the art, for example by hydrolysis, hydrogenolysis, alkaline saponification of esters with alkali in aqueous-alcoholic solution at temperatures of 0° to 50° C., acid saponification with mineral acids or in the case of, e.g., tert-butyl esters with the aid of trifluoroacetic acid.

As hydroxy protective groups, all those are suitable which can be easily introduced and later also easily cleaved again with reformation of the ultimately desired free hydroxy group. Preferred protective groups are ether groups, such as, e.g., the benzyl, 4-methoxybenzyl, 4-nitrobenzyl, di-and triphenylmethyl, trimethylsilyl, dimethyl-t-butylsilyl, diphenyl-t-butylsilyl group.

The hydroxy groups can also be present, e.g., as THP-ethers, α-alkoxyethylethers, MEM-ethers or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The cleavage of the hydroxy protective groups takes place in a way known in the art, e.g., in the case of a benzyl ether, by reductive cleavage with lithium/ammonia or by hydrogenolytic cleavage in the presence of, e.g., palladium-carbon, in the case of an ester, e.g., by alkaline saponification in aqueous-alcoholic solution at temperatures of 0° to 50° C. or in the case of tert-butyl esters with the aid of trifluoroacetic acid, as well as in the case of an ether or ketal cleavage by acid treatment with the aid of, e.g., cation exchangers, trifluoroacetic acid or mineral acids [see, e.g., "Protective Groups in Organic Synthesis," T. W. Greene, John Wiley and Sons (1981)].

As an example for an activated carboxy group, anhydride, p-nitrophenyl ester and acid chloride can be mentioned.

The reaction of the p-fluoroanilines of general formula II with the chlorosulfonyl derivatives of general formula III takes place in the presence of acid traps, such as, for example, tertiary amines (e.g., triethylamine, pyridine, N,N-dimethylaminopyridine, 1,5-diazabicyclo-[4.3.0]-nonene-5, 1,5-diazabicyclo-[5.4.0]-undecene-5), alkali or alkaline-earth carbonates or hydrogen carbonates, for example, of sodium, potassium, lithium, magnesium, calcium or barium. As solvents, e.g., dioxane, dichloroethane, dichloromethane or else tetrahydrofuran or dimethoxyethane are suitable. The reactions take place in the temperature range of −20° C. to 50° C., preferably at −5° C. to 20° C.

Then, as needed, the protective groups are removed to get directly to the end product or to an intermediate compound, which can be reacted to the end product, for example to an acid, which can be converted to the amide. Acid groups can optionally be salinized with organic or inorganic bases.

The compounds of general formula II can be obtained in a known way by a) reduction of the hydrogenation of corresponding nitro compounds IV

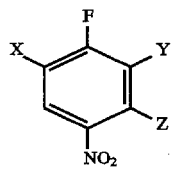     (IV)

or by proton-catalyzed saponification of the BOC derivatives of the amino compounds of general formula V

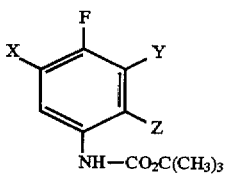

As proton source, in this case, trifluoroacetic acid is especially suitable.

As reducing agent, tin(II) chloride in acetic acid solution or else iron(II) sulfate in ammoniacal solution are suitable. The hydrogenation is advantageously performed in the presence of palladium on carbon. In this case, Pearlman's catalyst, palladium hydroxide 20% on carbon, has proven especially suitable.

Compounds of general formula IV are available by nitration of the compounds of Formula VI

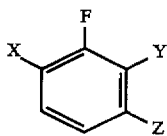

As nitrating agents, the mixture of sulfuric acid and nitric acid is used, but also the system of nitroethane/nitric acid/trifluoromethanesulfonic acid/phosphorus pentoxide described by G. Olah [Synthesis, 1087, (1992)]. Compounds of formula VI are available as commercial products or can be produced easily from the also commercially available compounds of formula VII

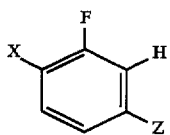

The already mentioned compounds of Formula V can also be produced from a commercially available precursor (VIII):

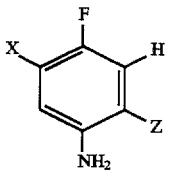

First, by reaction with a suitable BOC derivative, for example, the pyrocarbonate, an N-protected compound of formula IX is produced:

These compounds can be easily regioselectively metalated with n-butyllithium according to the method of M. Schlosser [Synlett, 360 (1992)] and then converted to compounds of formula V by reaction with electrophiles.

Compounds of formula III are directly available as commercial products (e.g., $ClSO_2CF_3$, $ClSO_2CH_2CF_3$, $ClSO_2CH_2CO_2CH_3$) or can be produced from commercially available precursors.

Starting from disulfide dicarboxylic acid esters, by oxidation with elementary chlorine under hydrolyzing conditions in high yields, a simpler synthesis method directly provides sulfonyl chloride:

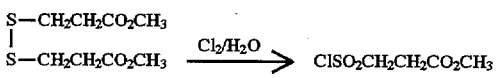

If the compounds of general formula I in the sulfonamide part have an amide structure If the compounds of general formula I in the sulfonamide part have an amide structure

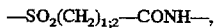

then it often proves easy to produce first a compound of structure

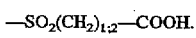

The reaction of these acid groups as well as the additional acid groups optionally present in the molecule to the corresponding amides takes place according to methods known in the literature, e.g., in the presence of reagents, such as carbonyldiamidazole, carbodiimide, preferably dicyclohexylcarbodiimide (DCC), (e.g., Am. Soc. 81, 890) in aprotic solvents, such as, e.g., dimethylformamide, dioxane, dichloromethane or their mixtures at temperatures of $-10°$ C. to $100°$ C., preferably $-10°$ C. to room temperature, within 1 to 24, preferably 2 to 12 hours.

The linkage of the amide bonds can also take place by aminolysis of activated carboxyl groups (e.g., as mixed anhydride).

Thus, the aminolysis of, e.g., esters takes place in liquid phase, e.g., in a suitable higher-boiling solvent, such as dimethylformamide, dimethylacetamide or dimethyl sulfoxide. The reaction temperatures are approximately $20°$ C.–$200°$ C., and temperatures of $100°$–$180°$ C. are preferred. The reaction times are between 2 hours and reaction tys, and reaction times between 4 hours and 36 hours are preferred.

Moreover, all methods for converting carboxyl groups to amide groups known to one skilled in the art can be used for synthesis of the p-fluorobenzenesulfonamides of general formula I, thus, e.g., the method according to Krejcarek and Tucker, Biochem. Biophys. Res. Commun. 77, 581 (1977) with mixed anhydrides.

Polyhydroxyalkylamines can advantageously also be used in protected form for reaction, e.g., as O-acyl derivatives or as ketals. This holds true especially if these derivatives can be produced more easily and more inexpensively than the polyhydroxyalkylamines themselves. A typical example is the 2-amino-1-(2,2-dimethyl-1,3-dioxolan-4-yl)-ethanol, the acetonide of the 1-amino-2,3,4-trihydroxybutane, produced according to DE-OS 31 50 917.

The subsequent removal of protective groups is problem-free and can take place, for example, by treatment with an acid ion exchanger in aqueous-ethanolic solution.

After production of the desired compound of general formula I, acid hydrogen atoms present in the molecule can be substituted by cations of inorganic and/or organic bases.

The neutralization takes place, in this case, with the aid of inorganic bases (for example, hydroxides, carbonates or bicarbonates) of, for example, sodium, potassium, lithium, magnesium and calcium and/or organic bases, such as, i.a., primary, secondary and tertiary amines, such as, for example, ethanolamine, morpholine, glucamine, N-methyl and N,N-dimethylglucamine.

For the production of neutral salts, an equivalent of the desired bases can be added, for example, to the acids in aqueous solution or suspension. The obtained solution can then be evaporated to dryness in a vacuum or freeze-dried. Often, it is advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus to obtain easily isolated and readily purified crystallizates.

If the acid compounds contain several free acid groups, it is often advisable to produce neutral mixed salts, which contain both inorganic and organic cations as counterions.

The production of the diagnostic agents according to the invention also takes place in a way known in the art, by the compounds according to the invention—optionally with the addition of the additives usual in galenicals—being suspended or dissolved in aqueous medium and then the suspension or solution optionally being sterilized. Suitable additives are, for example, physiologically harmless buffers (such as, for example, tromethamine), small additions of complexing agents (such as, for example, diethylenetriaminepentaacetic acid) or, if necessary, electrolytes, such as, for example, sodium chloride or, if necessary, antioxidants, such as, for example, ascorbic acid.

If suspensions or solutions of the agents according to the invention in water or physiological salt solution are desired for enteral administration or other purposes, they are mixed with one or more adjuvants usual in galenicals [for example, methylcellulose, lactose, mannitol] and/or surfactant(s) [for example, lecithins, Tween®, Myrj®] and/or flavoring substance(s) for taste correction (for example, ethereal oils).

The fluorine-containing compounds according to the invention can be used advantageously in vivo NMR diagnosis, i.e., for NMR imaging and in NMR spectroscopy as indicators of various parameters. Thus, i.a., with the aid of spectroscopy with high-sensitivity resolution and thus tissue-specific pH, $pO_2$, $pCO_2$, temperature, redox processes, reaction kinetics can be measured.

Further, it was determined that the compounds according to the invention are surprisingly distinguished by a very good compatibility.

The pharmaceutical agents according to the invention are preferably produced in a concentration of 1 µmol-1 mol/l. They are generally dosed in amounts of 0.005-20 mmol/kg of body weight, preferably 0.05-5 mmol/kg of body weight. They are intended for enteral and parenteral administration.

The agents according to the invention meet the varied requirements for suitability as diagnostic agents for NMR tomography and NMR spectroscopy and may be used in a manner analogous to such agents but exhibiting the described improvement. Further, they show the high effectiveness which is necessary to load the body with the smallest possible amounts of foreign substances and the good compatibility which is necessary to maintain the noninvasive nature of the studies.

In comparison to the structurally closest compounds of the prior art, the compounds according to the invention show clearly thinner signals for the measuring fluorine atom, so that an identically intensive signal is obtained with a smaller dosage. Thus, for example, the compound of Example 2 exhibits a line width smaller by 12%, that of Example 6 a line width smaller by 25%, in comparison to the structurally closer compound of the prior art (compound of Example 2 with Y meaning hydrogen), which in the case of Example 6 provides a signal increase of almost 50%.

The good water solubility of the agents according to the invention makes it possible to produce highly-concentrated solutions, thus to keep the volume load of the circulatory system within reasonable limits and to balance out the dilution by bodily fluid, i.e., NMR diagnostic agents must be 100-1000 times more water-soluble than the agents used in the in vitro NMR spectroscopy.

The biological properties of the compounds according to the invention are clearly better relative to the prior art; thus, for example, the compound of Example 2 exhibits a compatibility that is higher by 50% than the structurally closest previously-known compound (compound of Example 2 with Y meaning hydrogen). An equally high (undesirable) histamine release is observed with the compound of Example 2 only with the 30-fold dosage of the above-mentioned previously-known comparison substance.

The good compatibility of the compounds according to the invention allows the examination and NMR-spectroscopic measurement of pH in the living organism. In this case, an administration of 10 µmol/kg to 10 mmol/kg of body weight makes possible a problem-free determination of the change of the chemical shift of the $^{19}F$ signal relative to the reference signal (e.g., an intramolecular $CF_3$ group) and thus of the pH. The administered solution is dispersed quickly in the organism and is thus able to identify areas of different pH. A change of pH and thus optionally a therapeutic effect can, moreover, be produced by a corresponding dosage.

To be able to indicate small changes of pH, the compounds are advantageous whose pK is near the biological or pathological pH of the tissue of interest. Generally, those compounds whose pK lies between 2 and 9, preferably between 6 and 8, are of special interest. Compounds which indicate the pH of the gastrointestinal tract advantageously have a pK between 2 and 8. Since the greatest accuracy of the determination of pH exists in the range of the greatest change of the chemical shift per unit, thus with the pK of the respective compound, a very good analysis of biological processes is possible. Thus, the pH of blood is approximately 7.2–7.4; pathological areas can have a changed pH, which can drop, e.g., to 4.0 or lower.

For the visualization of the renal function or analysis of primary and secondary urine, compounds with a pK between 5 and 7 are advantageous, since the pH of urine generally lies below that of blood. For the determination of the intragastric pH, compounds which most clearly show a change of the chemical shift between pH 2 and 6 are advantageous, since the pH of the gastric juice can greatly fluctuate between almost 1 and 7.

By the use of the new type of fluorinated measuring probes with very good compatibility, it has thus been possible to perform spectroscopy with high-sensitivity resolution in smaller volumes (e.g., 10 ccm) and to determine physiologically important parameters, such as, e.g., the pH, precisely in shorter testing time without disturbance or superposition by other molecules.

The mentioned compounds are also suitable for in vivo imaging (NMR imaging). In this case, not only the data of the varying chemical shift are represented graphically, but the local concentrations of the fluorinated compounds are reproduced in an imaging by the imaging sequences usual in MRI. The advantage of the $_{19}F$ imaging relative to $^1H$ tomography is based on the fact that the dispersion of the pharmaceutical agent can be visualized directly without superposition by disruptive structures.

Thus, e.g., an excellent contrasting of the renal excretion system (kidney, ureter, bladder) is possible after intravenous administration of the compounds according to the invention, which are administered in a dose of 5 μmol/kg to 20 mmol/kg, preferably of 0.1 mmol/kg to 5 mmol/kg. In this case, it has surprisingly also been found that the additional injection of a paramagnetic compound (e.g., GdDTPA/ dimeglumine) in a dose of 1 μmol/kg to 2 mmol/kg, preferably of 50 μmol/kg to 500 μmol/kg, provides a clear improvement of image quality.

Coupled to macromolecules, for example, monoclonal antibodies, the compounds according to the invention can also be used as organ-specific and tumor-specific therapeutic agents and diagnostic agents.

The compounds of general formula I according to the invention are also to be used against all bacterial infections, which can be treated chemotherapeutically with sulfonamides.

The following examples are used for a more detailed explanation of the object of the invention:

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application P4447389.3, is hereby incorporated by reference.

EXAMPLE 1

2-{N-[4-Fluoro-2-trifluoromethylphenyl-3-acetic acid-N-(1-hydroxymethyl-2,3-dihydroxypropyl)- amide]-sulfonyl}-acetic acid a) 6-Fluoro-3-nitro-2-trifluoromethyl-phenylacetic acid 6.33 g (100.62 mmol) of fuming nitric acid (100%) and 25.80 g (91.44 mmol) of trifluoromethanesulfonic anhydride are mixed under ice bath cooling. 200 ml of nitroethane and 12.93 g (91.44 mmol) of phosphorus pentoxide are added to this mixture. 20.31 g (91.44 mmol) of 2-fluoro-6-trifluoromethylphenylacetic acid, suspended in 40 ml of nitroethane, is now instilled under cooling. It is stirred for 1 hour at 0° C. and then allowed to reach room temperature and stirred overnight at room temperature. The thin-layer chromatogram no longer shows starting material. The suspension is poured on 350 ml of cooled, saturated sodium bicarbonate solution. It is extracted three times with dichloromethane. Then, it is acidified with 4N hydrochloric acid, extracted five times with ethyl acetate. The organic phase is washed with water, dried on sodium sulfate and evaporated to dryness in a vacuum. The residue is crystallized from ether/pentane.

Yield: 16.81 g (68.8% of theory) Melting point: 180.3° C.

Elementary analysis: $C_9H_5F_4NO_4$ Cld: C 40.47 H 1.89 F 28.45 N 5.24 Fnd: C 40.55 H 1.93 F 28.40 N 5.30 b) 6-Fluoro-3-nitro-2-trifluoromethylphenylacetic acid-N-(5-hydroxy-2,2-dimethyl-1,3-dioxepan-6-yl)-amide 6.0 g (22.46 mmol) of the acid produced under Example 1a) is dissolved in 50 ml of absolute tetrahydrofuran. 3.64 g (22.46 mmol) of 1,1-carbonyldiimidazole is now added under nitrogen and with exclusion of moisture. It is allowed to stir for 1 more hour and then 3.64 g (22.46 mmol) of powdered 5-amino-2,2-dimethyl-1,3-dioxepan-6-ol is added to it, and it is allowed to stir overnight at room temperature. It is then evaporated to dryness in a vacuum, taken up in ethyl acetate, washed with 10% citric acid solution, with saturated sodium bicarbonate solution as well as water, dried on sodium sulfate and evaporated to dryness in a vacuum. The substance is purified by column chromatography on silica gel. Mixtures of ethyl acetate and ethanol are used as eluant. The title compound is obtained as foam.

Yield: 8.44 g (91.6% of theory)

Elementary analysis: $C_{16}H_{18}F_4N_2O_6$ Cld: C 46.84 H 4.42 F 18.52 N 6.83 Fnd: C 46.74 H 4.50 F 18.63 N 6.78 c) 6-Fluoro-2-trifluoromethyl-3-nitro-phenylacetic acid-N-(6-acetoxy-2,2-dimethyl-1,3-dioxepan-5-yl)-amide The mixture of 9.54 g (23.26 mmol) of the amide produced under 1b), 6 ml (74.2 mmol) of dry pyridine and a spatula-tip full of 4-dimethylaminopyridine in 20 ml of dry tetrahydropyran is instilled in a mixture of 2.6 ml (27.6 mmol) of acetic anhydride and 100 ml of absolute tetrahydrofuran with stirring and under cooling. After completion of the addition, it is allowed to stir for 1 more hour, then 10 ml of ethanol is added to it, allowed to stir for 30 more minutes, then evaporated to dryness in a vacuum, ethyl acetate is taken up and washed with 10% citric acid, then with saturated sodium bicarbonate solution, dried on sodium sulfate and evaporated to dryness in a vacuum. The title compound is obtained as crystals.

Yield: 9.40 g (89.6% of theory)

Elementary analysis: $C_{18}H_{20}F_4N_2O_7$ Cld: C 47.79 N 4.46 F 16.80 N 6.19 Fnd: C 47.77 N 4.34 F 16.71 N 6.15 d) 3-Amino-6-fluoro-2-trifluoromethyl-phenylacetic acid-N-(6-acetoxy-2,2-dimethyl-1,3-dioxepan-5-yl)-amide 10.00 g (22.11 mmol) of the nitro compound produced under Example 1c) is dissolved in 350 ml of ethanol and mixed with 0.8 g of Pearlman's catalyst (Pd 20%, C.). It is evacuated until foaming no longer takes place, aerated with hydrogen and hydrogenated until 1485 ml (66.3 mmol) of hydrogen is taken up. It is suctioned off from the catalyst, rewashed well with ethanol and the solution is evaporated to dryness in a vacuum.

Yield: 8.82 g (94.4% of theory)

Elementary analysis: $C_{18}H_{22}F_4N_2O_5$ Cld: C 50.53 H 5.30 F 19.98 N 7.34 Fnd: C 50.41 H 5.37 F 20.09 N 7.41 e) 2-{N-[4-Fluoro-2-trifluoromethylphenyl-3-acetic acid-N-(6-acetoxy-2,2-dimethyl-1,3-dioxepan-5-yl)-amide]-sulfamoyl}-acetic acid methyl ester 9.34 g (22.11 mmol) of the amino compound produced under 1d) is dissolved in 120 ml of dichloromethane. 24 ml of absolute pyridine as well as 100 mg of 4-dimethylaminopyridine are added to it and cooled off to 0° C. 4.06 g (22.11 mmol) of chlorosulfonylacetic acid methyl ester, dissolved in 10 ml of dichloromethane, is now instilled under cooling. It is allowed to stir for 1 hour at 0° C., then overnight at room temperature. It is diluted with dichloromethane, washed with 10% citric acid solution, with saturated sodium bicarbonate solution as well as water. After drying on sodium sulfate, it is evaporated to dryness in a vacuum. The residue is purified by chromatography on silica gel. A mixture of ethyl acetate and hexane is used as eluant. The title compound crystallizes from ethyl acetate/hexane.

Yield: 7.66 g (62.0% of theory) Melting point: 172°–74° C.

Elementary analysis: $C_{21}H_{26}F_4N_2O_9S$ Cld: C 45.16 H 4.69 F 13.61 N 5.02 S 5.74 Fnd: C 45.17 H 4.58 F 13.77 N 4.93 S 5.50 f) 2-{N-[4-Fluoro-2-trifluoromethylphenyl-3-acetic acid-N-(1-hydroxymethyl-2,3-dihydroxypropyl)-amide]-sulfamoyl}-acetic acid 6.70 g (12 mmol) of the compound produced under Example 1e) is suspended in 50 ml of ethanol. It is mixed with 18 ml (36 mmol) of 2N sodium hydroxide solution, heated briefly in a water bath and stirred overnight at room temperature. Then, it is evaporated to dryness in a vacuum, the residue is dissolved in ethanol/water, mixed with 34 ml of ion exchanger $H^+$ and stirred briefly. The solution shows a pH of 4. It is filtered from the exchanger, rewashed with ethanol and concentrated by evaporation in a vacuum. It is taken up in distilled water, mixed again with acid ion exchanger and heated in a water bath. It is then allowed to stir overnight at room temperature, filtered off from the exchanger, rewashed well with distilled water and the title compound is obtained by freeze-drying. The title compound is a foam.

Yield: 5.39 g (97.1% of theory)

Elementary analysis: $C_{15}H_{18}F_4N_2O_8S$ Cld: C 38.97 H 3.92 F 16.43 N 6.06 S 6.93 Fnd: C 39.12 H 3.98 F 16.29 N 6.00 S 6.90

EXAMPLE 2

3-{N-[4-Fluoro-2-trifluoromethylphenyl-3-acetic acid-N-(1-hydroxy-2,3-dihydroxypropyl)-amide]-sulfamoyl}-propionic acid a) 3-{N-[4-Fluoro-2-trifluoromethylphenyl-3-acetic acid-N-(6-acetoxy-2,2-dimethyl-1,3-dioxepan-5-yl)-amide]-sulfamoyl}-propionic acid methyl ester 7.60 g (22.11 mmol) of the amino compound, produced under 1d), is reacted in 120 ml of dichloromethane analogously to Example 1e) with 24 ml of absolute pyridine, 100 mg of 4-dimethylaminopyridine as well as 4.13 g (22.11 mmol) of 3-chlorosulfonylpropionic acid methyl ester and worked up. The title compound is obtained as crystals from ethyl acetate/hexane.

Yield: 7.99 g (63.1% of theory) Melting point: 146°–148° C.

Elementary analysis: $C_{22}H_{28}F_4N_2O_9S$ Cld: C 46.15 H 4.93 F 13.27 N 4.89 S 5.60 Fnd: C 46.22 H 4.98 F 13.22 N 4.96 S 5.52 b) 3-{N-[4-Fluoro-2-trifluoromethylphenyl-3-acetic acid-N-(1-hydroxy-2,3-dihydroxypropyl)-amide]-sulfamoyl}-propionic acid 5.73 g (10 mmol) of the compound produced under 2a) is dissolved in 100 ml of ethanol. It is mixed with 15 ml of 2N (30 mmol) sodium hydroxide solution, heated briefly in a water bath and stirred overnight at room temperature. Then, 25 ml of ion exchanger H$^+$ (1.5 meq/ml, 37.5 mmol) is added to it and heated for 90 minutes to 60°–70° C. with stirring. Starting material is no longer present. It is filtered from the exchanger, rewashed with water, concentrated by evaporation in a vacuum to a syrup and taken up again in distilled water. The title compound is obtained by freeze-drying as hygroscopic foam.

Yield: 4.40 g 992.4% of theory)

Elementary analysis: $C_{16}H_{20}F_4N_2O_8S$ Cld: C 40.34 H 4.23 F 15.95 N 5.88 S 6.73 Fnd: C 40.40 H 4.29 F 16.01 N 5.94 S 6.68

EXAMPLE 3

3-{N-[4-Fluoro-2-trifluoromethylphenyl-3-carbamoylmethyl]-sulfamoyl}-propionic acid a) 2-Fluoro-6-trifluoromethyl-phenylacetamide 20 g (98.5 mmol) of 2-fluoro-6-trifluoromethyl-phenyl-acetonitrile is dissolved in 150 ml of methanol. It is adjusted to pH 10 with sodium hydroxide solution and heated to 40° C. Then, 15 ml (132.3 mmol) of hydrogen peroxide (30%) is instilled, diluted with 25 ml of water, and the pH is kept between 9–10 by simultaneous addition of sodium hydroxide solution. A solid precipitates with foaming. After completion of the addition, it is stirred for 30 more minutes, allowed to cool off, suctioned off from the solid, washed with water and dried in a vacuum. The title compound is obtained in crystalline form.

Yield: 12.64 g (58.0% of theory)

Melting point: 172°–174° C.

Elementary analysis: $C_9H_7F_4NO$ Cld: C 48.88 H 3.19 F 34.36 N 6.33 Fnd: C 49.01 H 3.25 F 34.40 N 6.30 b) 6-Fluoro-3-nitro-2-trifluoromethyl-phenylacetamide 1.37 ml (33.3 mmol) of fuming nitric acid (100%) and 10 g (66.7 mmol) of trifluoromethanesulfonic acid are added to 60 ml of nitroethane under ice cooling and with exclusion of moisture. Then, 14.22 g (100.05 mmol) of phosphorus pentoxide is added to this mixture. Under further cooling, the amide (7.36 g, 33.3 mmol) produced under Example 3a) is now added in portions under further cooling. Stirring is allowed to continue over the weekend at room temperature. It is cooled again to 0° C., and ice/ice water is added to it. Then, it is diluted with dichloromethane, the organic phase is separated, washed with saturated sodium bicarbonate solution and then with water. It is dried on sodium sulfate, concentrated by evaporation in a vacuum and the title compound is obtained as solid.

Yield: 5.91 g (66.7% of theory)

Elementary analysis: $C_9H_6F_4N_2O_3$ Cld: C 40.62 H 2.27 F 34.36 N 6.33 Fnd: C 40.71 H 2.33 F 34.31 N 6.40 c) 3-Amino-6-fluoro-2-trifluoromethyl-phenylacetamide 5.32 g (20 mmol) of the nitro compound produced under 3b) as well as 0.40 g of Pearlman's catalyst (Pd 20%, C.) are added to 250 ml of ethanol. It is evacuated and aerated, when the foaming drops off, with hydrogen. It is hydrogenated until 1344 ml (60 mmol) of hydrogen is taken up. Then, it is suctioned off from the catalyst, the latter is rewashed well with ethanol and the combined solutions are concentrated by evaporation in a vacuum. The title compound is obtained as white solid.

Yield: 4.55 g (96.3% of theory)

Elementary analysis: $C_9H_8F_4N_2O$ Cld: C 45.77 H 3.41 F 32.18 N 11.86 Fnd: C 45.70 H 3.49 F 32.25 N 11.91 d) 3-{N-[4-Fluoro-2-trifluoromethylphenyl-3-carbamoylmethyl]-sulfamoyl}-propionic acid methyl ester 2.36 g (10 mmol) of the amino compound produced under Example 3c) is dissolved in 100 ml of dichloromethane. Then, 12 ml of dry pyridine as well as a spatula-tip full of 4-dimethylaminopyridine are added to it. 2.05 g (11 mmol) of 3-chlorosulfonylpropionic acid methyl ester is now instilled in it under cooling and allowed to stir overnight at room temperature. It is then shaken out with 2N hydrochloric acid, rewashed with saturated sodium bicarbonate solution, dried on sodium sulfate and evaporated to dryness in a vacuum. The title compound is obtained as foam, which is chromatographed for purification on silica gel. A mixture of ethyl acetate and ethanol is used as eluant.

Yield: 2.50 g (64.7% of theory)

Elementary analysis: $C_{13}H_{14}F_4N_2O_5S$ Cld: C 40.42 H 3.65 F 19.67 N 7.25 S 8.30 Fnd: C 40.34 H 3.70 F 19.77 N 7.31 S 8.24 e) 3-{N-[4-Fluoro-2-trifluoromethylphenyl-3-carbamoylmethyl]-sulfamoyl}-propionic acid 3.86g (10 mmol) of the ester produced under Example 3d) is dissolved in 100 ml of ethanol. 10 ml (20 mmol) of 2N sodium hydroxide solution is added to the solution, heated briefly in a water bath and allowed to stir overnight at room temperature. The thin-layer chromatogram no longer shows starting material. It is adjusted with acid ion exchanger to pH 4, suctioned off from resin, rewashed well with water and concentrated by evaporation in a vacuum. The residue is replaced, taken up in distilled water and subjected to freeze-drying. The title compound is obtained as hygroscopic foam.

Yield: 3.45 g (92.8% of theory)

Elementary analysis: $C_{12}H_{12}F_4N_2O_5S$ Cld: C 38.71 H 3.25 F 20.41 N 7.52 S 8.61 Fnd: C 38.79 H 3.33 F 20.34 N 7.60 S 8.54

EXAMPLE 4

3-{N-[4-Fluoro-2-trifluoromethylphenyl-3-carboxymethyl]-sulfamoyl}-propionic acid a) 2-Fluoro-6-trifluoromethyl-phenylacetic acid methyl ester 4 ml of concentrated hydrochloric acid and 10 g (49.2 mmol) of 2-fluoro-6-trifluoromethylphenylacetic acid nitrile are dissolved in 100 ml of methanol. It is then refluxed for 3 hours, concentrated by evaporation in a vacuum to one third, cooled off and diluted with 300 ml of dichloromethane. It is then shaken out with water and with saturated sodium bicarbonate solution, the solution is dried on sodium sulfate, and it is concentrated by evaporation in a vacuum.

The title compound is obtained as solid.

Yield: 10.41 g (89.6% of theory)

Elementary analysis: $C_{10}H_8F_4N_2O_2$ Cld: C 50.86 H 3.41 F 32.18 Fnd: C 50.92 H 3.45 F 32.09 b) 6-Fluoro-3-nitro-2-trifluoromethyl-3-nitro-phenylacetic acid methyl ester 1.37 ml (33.3 mmol) of fuming nitric acid (100%) and 10 g (33.3 mmol) of trifluoromethanesulfonic acid as well as 14.22 g (100.05 mmol) of phosphorus pentoxide are added to 40 ml of nitroethane with stirring and under cooling. Then, the ester, produced under Example 4a), in 10 ml of nitroethane, is dissolved slowly in it and allowed to stir for 60 hours at room temperature. It is now cooled to 0° C. and ice/ice water is added to it, mixed with dichloromethane and the phases are separated. The organic phase is washed with sodium bicarbonate solution and water, dried on sodium sulfate and concentrated by evaporation in a vacuum. The title compound is obtained as oil.

Yield: 64.25 g (64.25g % of theory)

Elementary analysis: $C_{10}H_7F_4NO_4$ Cld: C 42.72 H 2.51 F 27.03 N 4.98 Fnd: C 42.78 H 2.55 F 27.00 N 5.04 c) 3-Amino-6-fluoro-2-trifluoromethyl-phenylacetic acid methyl ester 6.8 g (30 mmol) of tin(II) chloride, dihydrate, is dissolved with heating in 40 ml of glacial acetic acid. During cooling, a fine suspension results. The nitro compound obtained under Example 4b), 2.81 g (10 mmol) dissolved in 10 ml of glacial acetic acid, is instilled in the latter. After a brief continuation of stirring, a thin-layer chromatogram is prepared. It shows that starting material is no longer present and that only one product was produced. The clear yellow solution is concentrated by evaporation in a vacuum. The residue is dissolved in dichloromethane, the solution is washed with saturated sodium bicarbonate solution, dried on sodium sulfate and concentrated by evaporation in a vacuum. The title compound is obtained as foam.

Yield: 2.21 g (88.0% of theory)

Elementary analysis: $C_{10}H_9F_4NO_2$ Cld: C 47.82 H 3.61 F 30.25 N 5.58 Fnd: C 47.78 H 3.66 F 30.30 N 5.62 d) 3-{N-[4-Fluoro-2-trifluoromethylphenyl-3-acetic acid methyl ester]-sulfonyl}-propionic acid methyl ester 2.51 g (10 mmol) of the amino compound produced under Example 4c) is dissolved in 50 ml of dichloromethane and 9 ml of dry pyridine. It is cooled off to −5° C. and then 1.87 g (10 mmol) of 3-chlorosulfonylpropionic acid methyl ester, dissolved in 10 ml of dichloromethane, is distilled in it. It is allowed to thaw and stirred overnight at room temperature. Then, it is diluted with dichloromethane, rewashed with 2N hydrochloric acid as well as saturated sodium bicarbonate solution, dried on sodium sulfate and evaporated to dryness in a vacuum. The product is purified by chromatography on silica gel. A mixture of ethyl acetate and hexane is used as eluant. The title compound is obtained as foam.

Yield: 2.56 g (63.8% of theory)

Elementary analysis: $C_{14}H_{15}F_4NO_6S$ Cld: C 41.90 H 3.77 F 18.94 N 3.49 S 7.99 Fnd: C 41.98 H 3.86 F 18.98 N 3.52 S 7.92 e) 3-[N-(4-Fluoro-2-trifluoromethylphenyl-3-acetic acid)-sulfamoyl]-propionic acid 1.99 g (5 mmol) of the compound obtained under Example 4d) is dissolved in 10 ml of ethanol. It is mixed with 10 ml (20 mmol) of 2N sodium hydroxide solution, heated briefly in a water bath and allowed to stir overnight at room temperature. According to a thin-layer chromatogram, starting material is no longer present. It is substantially concentrated by evaporation in a vacuum, taken up in distilled water, the solution is mixed with ion exchanger $H^+$ until the pH has dropped to 4, suctioned off from the exchanger, rewashed well with water and substantially concentrated by evaporation in a vacuum. It is diluted again with water and the title compound is obtained by freeze-drying. The substance is obtained as foam.

Yield: 1.71 g (91.6% of theory)

Elementary analysis: $C_{12}H_{11}F_4NO_6S$ Cld: C 38.61 H 2.97 F 20.36 N 3.75 S 8.59 Fnd: C 38.72 H 3.06 F 20.42 N 3.80 S 8.63

EXAMPLE 5

N-{4-Fluorophenyl-3,5-bis[acetic acid-N-(1-hydroxymethyl-2,3-dihydroxypropyl)-amide]}-trifluoromethylsulfonamide a) 2-Fluorophenyl-1,3-bis(acetic acid methyl ester)

20 g (114.8 mmol) of 2-fluorophenyl-1,3-bis(acetic acid nitrile) is dissolved in 100 ml of methanol. After the addition of 5 ml (275.6 mmol) of water, it is cooled to −10° C. and hydrochloric acid is introduced until saturation. It is allowed to stir overnight at room temperature. Then, it is refluxed for 6 hours. It is evaporated to dryness in a vacuum, taken up in ethyl acetate, washed with water, dried on sodium sulfate and evaporated to dryness in a vacuum. The title compound is obtained as solid.

Yield: 26.45 g (95.9% of theory) Melting point: 58.6° C.

Elementary analysis: $C_{12}H_{13}FO_4$ Cld: C 60.00 H 5.45 F 7.91 Fnd: C 59.84 H 5.37 F 8.12 b) 2-Fluoro-phenyl-1,3-bis(acetic acid)

37.33 g (155.39 mmol) of the diester produced under Example 5a) is dissolved in 460 ml of dioxane. 163.2 ml (326.4 mmol) of 2N sodium hydroxide solution is added to it and heated briefly. It is allowed to stir overnight, evaporated to dryness in a vacuum, taken up in water and acidified with 2N hydrochloric acid. It is taken up in ethyl acetate, dried on sodium sulfate and concentrated by evaporation in a vacuum. The residue is recrystallized from ethyl acetate/hexane. The title compound is obtained as white crystals.

Yield: 28.64 g (86.9% of theory) Melting point: 177.5° C.

Elementary analysis: $C_{10}H_9FO_4S$ Cld: C 56.61 H 4.28 F 8.95 Fnd: C 56.47 H 4.42 F 8.77 c) 2-Fluoro-5-nitrophenyl-1,3-bis(acetic acid)

28.05 g (134.32 mmol) of the acid obtained under Example 5b) is added to a mixture of 78 ml of concentrated sulfuric acid and 10.16 ml of 65% nitric acid under cooling. It is allowed to stir for 3 more hours. The thin-layer chromatogram shows complete reaction. The batch is poured on ice/water, mixed with sodium chloride and extracted with ethyl acetate. The organic phase is dried on sodium sulfate and evaporated to dryness in a vacuum. The title compound is obtained in crystalline form. The recrystallization takes place from ethyl acetate/hexane.

Yield: 33.99 g (98.4% of theory) Melting point: 182° C.

Elementary analysis: $C_{10}H_8FNO_6$ Cld: C 46.70 H 3.14 F 7.39 N 5.45 Fnd: C 46.64 H 3.18 F 7.44 N 5.61 d) 2-Fluoro-5-nitrophenyl-1,3-bis[acetic acid-N-(6-hydroxy-2,2-dimethyl-1,3-dioxepan-5-yl)-amide]

5.14 g (20 mmol) of the compound produced under Example 5c) is dissolved in 150 ml of dry tetrahydrofuran. It is mixed under cooling with 8.24 g (20 mmol) of dicyclohexylcarbodiimide, allowed to stir for 30 minutes and then 5-amino-2,2-dimethyl-1,3-dioxepan-6-ol is added to it. It is allowed to stir for 24 hours, suctioned off, the filtrate is concentrated by evaporation in a vacuum, taken up in dichloromethane, washed with cold 10% citric acid solution, with saturated sodium bicarbonate solution and water, dried on sodium sulfate and concentrated, by evaporation in a vacuum. The title compound is obtained as foam.

Yield: 8.08 g (74.3% of theory) Melting point: 190.7° C. ethanol/hexane

Elementary analysis: $C_{24}H_{34}FN_3O_{10}$ Cld: C 53.03 H 6.30 F 3.50 N 7.73 Fnd: C 53.14 H 6.38 F 3.55 N 7.67 e) 5-Amino-2-fluoro-phenyl-1,3-bis[acetic acid-N-(6-hydroxy-2,2-dimethyl-1,3-dioxepan-5-yl)-amide]

5.44 g (10 mmol) of the compound produced under Example 5d) is dissolved in 200 ml of ethanol. 0.4 g of Pearlman's catalyst (Pd 20%, c) is added to it, evacuated until foaming stops, aerated with hydrogen and hydrogenated until 673 ml (30 mmol) of hydrogen is taken up. It is suctioned off from the catalyst, rewashed with ethanol, and the combined solutions are concentrated by evaporation in a vacuum. The title compound is obtained as foam.

Yield: 4.96 g (96.5% of theory)

Elementary analysis: $C_{24}H_{36}FN_3O_8S$ Cld: C 56.13 H 7.07 F 3.70 N 8.18 Fnd: C 56.23 H 7.14 F 3.76 N 8.12 f) N-{4-Fluorophenyl-3,5-bis[acetic acid-N-(6-hydroxy-2,2-dimethyl-1,3-dioxepan-5-yl)-amide]}-trifluoromethylsulfonamide 5.14 g (10 mmol) of the amino compound produced under Example 5e) is dissolved in a mixture of 30 ml of dichloromethane and 9.8 ml of dry pyridine. It is cooled to −5° C. and then 1.69 g (10 mmol) of trifluoromethanesulfonic acid chloride, dissolved in 10 ml of dichloromethane, is instilled. It is allowed to stir for 2 hours at the low temperature. The thin-layer chromatogram then no longer shows starting material. It is diluted with dichloromethane, washed with water, dried on sodium sulfate and evaporated to dryness in a vacuum. The residue is purified by chromatography on silica gel. A mixture of ethyl acetate and hexane is used as eluant. The title compound is obtained as foam.

Yield: 4.42 g (68.4% of theory)

Elementary analysis: $C_{25}H_{35}F_4N_3O_{10}S$ Cld: C 46.51 H 5.46 F 11.77 N 6.51 S 4.97 Fnd: C 46.60 H 5.51 F 11.83 N 6.44 S 5.06 g) N-{4-Fluorophenyl-3,5-bis[acetic acid-N-(1-hydroxymethyl-2,3-dihydroxypropyl-amide]}-trifluoromethylsulfonamide 6.46 g (10 mmol) of the compound produced under Example 5f) is dissolved in 100 ml of ethanol. It is mixed with 15 ml (30 mmol) of 2N sodium hydroxide solution, heated briefly in a water bath and allowed to stir overnight at room temperature. Then, 25 ml (37.5 mmol) of ion exchanger H$^+$ (1.5 meg/ml) is added and allowed to stir for one-half hour more. It is suctioned off from the exchanger, the latter is rewashed well with water and the combined solutions are concentrated by evaporation in a vacuum. It is taken up in distilled water and the product is obtained by freeze-drying. The title compound is obtained as hygroscopic foam.

Yield: 4.94 g (87.4% of theory)

Elementary analysis: $C_{19}H_{27}F_4N_3O_{10}S$ Cld: C 40.36 H 4.81 F 13.44 N 7.43 S 5.67 Fnd: C 40.44 H 4.87 F 13.51 N 7.37 S 5.60

EXAMPLE 6

N-{4-Fluorophenyl-3,5-bis[acetic acid-N-(1-hydroxymethyl-2,3-dihydroxypropyl-amide]}-2,2,2-trifluoroethylsulfonamide a) N-{4-Fluorophenyl-3,5-bis[acetic acid-N-(6-hydroxy-2,2-dimethyl-1,3-dioxepan-5-yl)-amide]}-2,2,2-trifluoromethylsulfonamide Analogously to Example 5f), 5.14 g (10 mmol) of the amino compound produced under Example 5e) in a mixture of 30 ml of dichloromethane and 9.8 ml of dry pyridine is reacted with 1.83 g (10 mmol) of 2-chlorosulfonyl-1,1,1-trifluoroethane and worked up. The title compound is obtained as foam.

Yield: 4.80 g (72.8% of theory)

Elementary analysis: $C_{26}H_{37}F_4N_3O_{10}S$ Cld: C 47.34 H 5.65 F 11.52 N 6.37 S 4.86 Fnd: C 47.43 H 5.71 F 11.59 N 6.41 S 4.82

N-{4-Fluorophenyl-3,5-bis[acetic acid-N-(1-hydroxymethyl-2,3-dihydroxypropyl-amide-]}-2,2,2-trifluoroethylsulfonamide.

Analogously to Example 5g), 3.30 g (5 mmol) of the compound produced under Example 6a), dissolved in 50 ml of ethanol, is saponified with 8 ml (16 mmol) of 2N sodium hydroxide solution and converted with 15 ml of ion exchanger H$^+$ (1.5 meg/ml) to the protective group-free compound. The title compound is obtained by freeze-drying as hygroscopic foam.

Yield: 2.54 g (87.7% of theory)

Elementary analysis: $C_{20}H_{29}F_4N_3O_{10}S$ Cld: C 41.45 H 5.04 F 13.11 N 7.25 S 5.53 Fnd: C 41.40 H 5.10 F 13.19 N 7.18 S 5.61

EXAMPLE 7

3-{N-[4-Fluoro-2-trifluoromethylphenyl-3-(2,3-dihydroxy-)propyl]-sulfamoyl}-propionic acid a) 4-Fluoro-2-trifluoromethyl-N-tert-butoxycarbonyl-aniline 17.91 g (100 mmol) of 4-fluoro-2-trifluoromethyl-aniline is dissolved in 200 ml of dry tetrahydrofuran. The solution of 43.65 g (200 mmol) of bis(tert-butoxy)-dicarbonate in 50 ml of dry tetrahydrofuran is instilled in this solution. It is allowed to stir overnight, then concentrated by evaporation in a vacuum and the 4-fluoro-2-trifluoromethyl-phenyl-(tert-butoxycarbonyl)-imide is obtained. The compound is purified by recrystallization from diethyl ether/hexane.

(Melting point: 88°–90° C.)

It is taken up in 250 ml of acetonitrile, mixed with a catalytic amount of magnesium perchlorate and heated for 3 hours to 50° C. It is concentrated by evaporation in a vacuum, taken up in diethyl ether, washed with water, dried on sodium sulfate and evaporated to dryness in a vacuum. The title compound is obtained as solid.

Yield: 25.89 g (92.7% of theory)

Melting point: 61°–62° C.

Elementary analysis: $C_{12}H_{13}F_4NO_2$ Cld: C 51.62 H 4.69 F 27.22 N 5.02 Fnd: C 51.56 H 4.74 F 27.17 N 5.13 b) 2-(3-Benzyloxy-2-hydroxy)-propyl-6-tert-butoxycarbonylamino-3-fluorobenzotrifluoride 1.149 g (9.9 mmol) of N,N,N,N-tetramethylethylenediamine is dissolved in 40 ml of dry tetrahydrofuran and cooled off to −70° C. under argon. Then, 12.0 ml (20.4 mmol) of 1.70N n-butyllithium is instilled at this temperature and stirred for 30 more minutes. The compound produced under Example 7a) (2.51 g, 9 mmol)l is dissolved in 5 ml of tetrahydrofuran and it is also instilled at low temperature. After 3 hours, the solution of 1.869 g (11.4 mmol) of benzylglycide ether in 5 ml of tetrahydrofuran at −65° to −70° C. is instilled and allowed to stir for 1 more hour at −70° C. and then overnight at room temperature. It is then poured in a mixture of ether and saturated common salt solution, stirred well and the organic phase is separated. It is dried on sodium sulfate, concentrated by evaporation in a vacuum and the substance is purified by chromatography on silica gel. A mixture of ethyl acetate and hexane is used as eluant. The title compound is obtained as oil.

Yield: 3.30 g (82.7% of theory)

Elementary analysis: $C_{22}H_{25}F_4NO_4$ Cld: C 59.59 H 5.68 F 17.14 N 3.16 Fnd: C 59.66 H 5.75 F 17.21 N 3.12 c) 2-(3-Benzyloxy-2-acetoxy)-propyl-6-tert-butoxy-carbonylamino-3-fluoro-benzotrifluoride 8.87 g (20 mmol) of the compound produced under Example 7b) is dissolved in 100 ml of dichloromethane. A spatula-tip full of 4-dimethylaminopyridine as well as 1.582 g (20 mmol) of pyridine are then added to it and then 1.57 g (20 mmol) of acetyl chloride in 10 ml of dichloromethane is instilled in it with stirring and under cooling. It is allowed to stir overnight at room temperature, dispersed between water and dichloromethane, the organic solution is washed with saturated sodium bicarbonate solution, dried on sodium sulfate and evaporated to dryness in a vacuum. The title compound is obtained as oil.

Yield: 8.96 g (92.3% of theory)

Elementary analysis: $C_{24}H_{27}F_4NO_5$ Cld: C 59.38 H 5.61 F 15.65 N 2.89 Fnd: C 59.51 H 5.68 F 15.70 N 2.86 d) 6-Amino-2-(3-benzyloxy-2-acetoxy)-propyl-3-fluoro-benzotrifluoride 4.86 g (10 mmol) of the compound produced under Example 7c) is dissolved in 100 ml of dichloromethane. Then, 1 ml of trifluoroacetic acid in 10 ml of dichloromethane is added to it, allowed to stir for 5 more minutes and then mixed with saturated sodium bicarbonate solution until the solution is reacted in an alkaline manner. The organic phase is separated, it is dried on sodium sulfate and evaporated to dryness in a vacuum. The title compound is obtained as oil.

Yield: 3.48 g (90.4% of theory)

Elementary analysis: $C_{19}H_{19}F_4NO_3$ Cld: C 59.22 H 4.97 F 19.72 N 3.63 Fnd: C 59.33 H 5.06 F 19.73 N 3.69 e) 3-{N-[4-Fluoro-2-trifluoromethylphenyl-3-(2-acetoxy-3-benzyloxy-propyl)-sulfamoyl}-propionic acid methyl ester Analogously to Example 1e), 3.85 g (10 mmol) of the amino compound, produced under Example 7d), in 60 ml of dichloromethane is dissolved and reacted in the presence of 0.791 g (10 mmol) of dry pyridine with 1.866 g of 3-chlorosulfonylpropynoic acid methyl ester and analogously worked up. The title compound is purified by chromatography on silica gel, and a mixture of ethyl acetate and hexane is used as eluant. The title compound is obtained as amorphous foam.

Yield: 3.35 g (62.6% of theory)

Elementary analysis: $C_{23}H_{25}F_4NO_7S$ Cld: C 51.59 H 4.71 F 14.19 N 2.62 S 5.99 Fnd: C 51.69 H 4.76 F 14.25 N 2.65 S 6.08 f) 3-{N-[4-Fluoro-2-trifluoromethylphenyl-3-(2,3-dihydroxy-propyl)]-sulfamoyl}-propionic acid Analogously to Example 1g), 5.36 g (10 mmol) of the compound, produced under Example 7e), in ethanol, is dissolved, mixed with 15 ml (30 mmol) of 2N sodium hydroxide solution, heated briefly in a water bath and stirred overnight at room temperature. It is then mixed with 20 ml (40 mmol) of ion exchanger H$^+$ (1.5 meg/ml), stirred for one-half hour, suctioned off from the exchanger, rewashed with ethanol and evaporated to dryness in a vacuum. The residue is taken up in 100 ml of ethanol, mixed with 0.4 g of Pearlman's catalyst (Pd 20%, c) and hydrogenated until 224 ml (10 mmol) of hydrogen is taken up. It is suctioned off from the catalyst, rewashed with ethanol and the solution is evaporated to dryness in a vacuum. The residue is taken up in distilled water and subjected to freeze-drying. The title compound is obtained as hygroscopic foam.

Yield: 3.14 g (80.7% of theory)

Elementary analysis: $C_{13}H_{15}F_4NO_6S$ Cld: C 41.11 H 3.88 F 19.52 N 3.60 S 8.24 Fnd: C 40.04 H 3.93 F 19.61 N 3.66 S 8.17

EXAMPLE 8

3-{N-[4-Fluoro-2-trifluoromethylphenyl-3-(2-hydroxy-1-methoxy-ethyl]-sulfamoyl}-propionic acid a) 3-Fluoro-2-(1-hydroxy-2-methoxy)-ethyl-benzoic acid trifluoride Analogously to Example 7b), 3.28 g (20 mmol) of 3-fluoro-benzotrifluoride in 35 ml of dry tetrahydrofuran is reacted in the presence of 2.56 g (22.0 mmol) of N,N,N,N-tetramethylethylenediamine with 28.5 ml (45.60 mmol) of 1.6N n-butyllithium in hexane and then with 1.73 g (23.3 mmol) of dry methanol-free methoxyacetaldehyde in 10 ml of tetrahydrofuran. It is worked up analogously to Example 7b), and after chromatography on silica gel, in which a mixture of ethyl acetate and hexane is used as eluant, the title compound is obtained as amorphous foam.

Yield: 2.73 g (57.2% of theory)

Elementary analysis: $C_{10}H_{10}F_4O_2$ Cld: C 50.43 H 4.23 F 31.91 Fnd: C 50.52 H 4.31 F 31.86 b) 2-(2-Acetoxy-1-methoxy)-ethyl-3-fluoro-benzoic acid trifluoride 15 mmol of the compound produced under Example 8a) is dissolved in 60 ml of dichloromethane. 1.19 g (15 mmol) of dry pyridine as well as a spatula-tip full of 4-dimethylaminopyridine are added to it and then 1.18 g (15 mmol) of acetyl chloride in 10 ml of dichloromethane is instilled in it under cooling. After stirring overnight, it is washed with water and sodium bicarbonate. The solution is dried on sodium sulfate and evaporated to dryness in a vacuum. The title compound is obtained as oil.

Yield: 4.02 g (95.6% of theory)

Elementary analysis: $C_{12}H_{12}F_4O_3$ Cld: C 51.44 H 4.32 F 27.12 Fnd: C 51.52 H 4.40 F 27.16 c) 2-(2-Acetoxy-1-methoxy)-ethyl-3-fluoro-6-nitro-benzoic acid trifluoride

Analogously to Example 4b), the compound produced under 8b) is nitrated. 10 g (33.3 mmol) of trifluoromethanesulfonic acid, 1.37 ml (33.3 mmol) of fuming nitric acid (100%) as well as 14.22 g (100.95 mmol) of phosphorus pentoxide are introduced in 40 ml of nitroethane. Then, 9.33 g (33.3 mmol) of benzotrifluoride in 10 ml of nitroethane is added to it. The procedure is as further described under Example 4b). The title compound is obtained as oil.

Yield: 8.97 g (82.8% of theory)

Elementary analysis: $C_{12}H_{11}F_4NO_5$ Cld: C 44.32 H 3.41 F 23.37 N 4.31 Fnd: C 44.26 H 3.45 F 23.46 N 4.35 d) 6-Amino-2-(2-acetoxy-1-methoxy)-ethyl-3-fluoro-benzoic acid trifluoride 6.8 g of tin(II) chloride, dihydrate, is dissolved warm in 40 ml of glacial acetic acid. It is cooled to room temperature and then the solution of 3.25 g (10 mmol) of the nitro compound, produced under Example 8c), in 10 ml of glacial acetic acid is instilled in it. The stirring is allowed to continue briefly, then it is evaporated to dryness in a vacuum and the residue is extracted with dichloromethane. The organic solution is dried on sodium sulfate and evaporated to dryness in a vacuum. The title compound can be obtained as thin-layer chromatographically uniform oil.

Yield: 2.29 g (77.4% of theory)

Elementary analysis: $C_{12}H_{13}F_4NO_3$ Cld: C 48.82 H 4.44 F 25.74 N 4.74 Fnd: C 48.93 H 4.49 F 25.62 N 4.77 e) 3-{N-[4-Fluoro-2-trifluoromethylphenyl-3-(2-acetoxy-1-methoxy-ethyl]-sulfamoyl}-propionic acid methyl ester 2.95 g (10 mmol) of the amino compound produced under Example 8d) is dissolved in a mixture of 50 ml of dichloromethane and 9 ml of dry pyridine. After cooling to 0° C., the solution of 1.87 g (10 mmol) of 3-chlorosulfonylpropionic acid methyl ester is then instilled in it. It is allowed to reach room temperature and stirred overnight. Then, it is diluted with dichloromethane, the pyridine is washed with 2N hydrochloric acid, rewashed with saturated sodium bicarbonate solution, dried on sodium sulfate and evaporated to dryness in a vacuum. The purification takes place by chromatography on silica gel, and a mixture of ethyl acetate and hexane is used as eluant. The title compound is obtained as oil.

Yield: 2.83 g (63.5% of theory)

Elementary analysis: $C_{16}H_{19}F_4NO_7S$ Cld: C 43.15 H 4.30 F 17.06 N 3.14 S 7.20 Fnd: C 43.22 H 4.36 F 17.01 N 3.18 S 7.28 f) 3-{N-[4-Fluoro-2-trifluoromethylphenyl-3-(2-hydroxy-1-methoxy-ethyl]-sulfamoyl}-propionic acid 4.45 g (10 mmol) of the compound produced under Example 8e) is dissolved in 100 ml of ethanol. 15 ml (30 mmol) of 2N sodium hydroxide solution is added to it, it is heated briefly in a water bath and allowed to stir overnight at room temperature. Then, it is mixed with 25 ml (37.5 mmol) of ion exchanger $H^+$ (1.5 meg/ml), stirred for 30 more minutes, filtered off from the exchanger, rewashed well with water and evaporated to dryness in a vacuum. The concentration by evaporation of the aqueous solution is repeated, then taken up again in distilled water and subjected to freeze-drying. The title compound is obtained as foam.

Yield: 3.00 g (84.8% of theory)

Elementary analysis: $C_{10}H_{15}F_4NO_6S$ Cld: C 34.00 H 4.28 F 21.51 N 3.96 S 9.08 Fnd: C 34.09 H 4.36 F 21.44 N 4.00 S 9.16

EXAMPLE 9

3-{N-[4-Fluoro-2-trifluoromethyl-3-benzoic acid-N-bis(2-hydroxyethyl)-amide]-sulfamoyl}-propionic acid methyl ester a) 6-Fluoro-3-nitro-2-trifluoromethyl-benzoic acid 1.05 ml (23.3 mmol) of concentrated nitric acid (65%), which also was precooled to 0° C., is instilled in a solution of 17.5 ml of concentrated sulfuric acid and 2.5 g (12.0 mmol) of 2-fluoro-6-trifluoromethyl-benzoic acid, cooled to 0° C. It is allowed to stir for one more hour at 0° C. and then overnight at room temperature. It is then poured in a mixture of ice, water and dichloromethane, the organic phase is separated and the aqueous phase is extracted with dichloromethane. The organic solutions are combined, washed with saturated sodium chloride solution, dried on sodium sulfate and evaporated to dryness in a vacuum. The title compound is obtained in crystalline form.

Yield: 1.95 g (64.2% of theory) Melting point: 190° C.

Elementary analysis: $C_8H_3F_4NO_4$ Cld: C 37.96 H 1.19 F 30.02 N 5.53 Fnd: C 38.00 H 1.25 F 30.09 N 5.60 b) 6-Fluoro-3-nitro-2-trifluoromethyl-benzoic acid-bis(2-hydroxyethyl)-amide 2.53 g (10 mmol) of the acid produced according to Example 9a) is dissolved in 100 ml of dry tetrahydrofuran. It is cooled to 0° C. and 1.622 g (10 mmol) of carbonyldiimidazole is added to it. After one hour of stirring at 0° C., 1.051 g (10 mmol) of diethanolamine in 3 ml of tetrahydrofuran is added to it and then allowed to stir overnight at room temperature. It is then evaporated to dryness in a vacuum, taken up in dichloromethane, washed with 2N hydrochloric acid, saturated common salt solution, dried on sodium sulfate and then evaporated to dryness in a vacuum. The purification of the compound takes place by chromatography on silica gel. A mixture of ethyl acetate and ethanol is used as eluant. The title compound is obtained as oil.

Yield: 1.58 g (76.3% of theory)

Elementary analysis: $C_{12}H_{12}F_4N_2O_5$ Cld: C 42.36 H 3.55 F 22.34 N 8.23 Fnd: C 42.42 H 3.61 F 22.28 N 8.15 c) 6-Fluoro-3-nitro-2-trifluoromethyl-benzoic acid-bis(2-acetoxyethyl)-amide 6.81 g (20 mmol) of the compound produced under Example 9c) is dissolved in 100 ml of dichloromethane and mixed with 3.32 g (42 mmol) of dry pyridine. It is cooled to 0° C. and then 3.30 g (42 mmol) of acetyl chloride, dissolved in 20 ml of dichloromethane, is instilled. After stirring overnight, the solution is washed with 2N hydrochloric acid, saturated sodium bicarbonate solution, it is dried on sodium sulfate and evaporated to dryness in a vacuum. The title compound is obtained as viscous oil. Yield: 7.49 g (88.3% of theory)

Elementary analysis: $C_{16}H_{16}F_4N_2O_7$ Cld: C 45.29 H 3.80 F 17.91 N 6.60 Fnd: C 45.22 H 3.85 F 17.99 N 6.64 d) 3-Amino-6-fluoro-2-trifluoromethyl-benzoic acid-bis(2-acetoxyethyl)-amide 8.49 g (20 mmol) of the nitro compound described under Example 9c) is dissolved in 200 ml of ethanol. It is mixed with 0.8 g of Pearlman's catalyst (Pd 20%, c), evacuated until the foam has flattened out, aerated with hydrogen and hydrogenated until 1344 ml (60 mmol) of hydrogen is taken up. It is suctioned off from the catalyst, rewashed well with ethanol and the combined solutions are evaporated to dryness in a vacuum. The title compound is obtained as viscous oil.

Yield: 7.32 g (92.8% of theory)

Elementary analysis: $C_{16}H_{18}F_4N_2O_5$ Cld: C 48.74 H 4.60 F 19.27 N 7.10 Fnd: C 48.86 H 4.71 F 19.40 N 7.19 e) 3-{N-[4-Fluoro-2-trifluoromethyl-3-benzoic acid-N-bis(2-acetoxyethyl)-amide]-sulfamoyl}-propionic acid methyl ester 3.943 g (10 mmol) of the amino compound produced under Example 9d) is dissolved in 100 ml of dichloromethane. 0.791 g (10 mmol) of dry pyridine is added to it, cooled to −5° C. and then 1.866 g (10 mmol) of 3-chlorosulfonylpropionic acid methyl ester, dissolved in 10 ml of dichloromethane, is instilled in it. It is stirred for 1 more hour at the low temperature, then for 12 more hours at room temperature. After dilution with dichloromethane, it is washed with 2N hydrochloric acid, with saturated sodium bicarbonate solution and then dried on sodium sulfate. It is evaporated to dryness in a vacuum and the residue is subjected to a chromatography on silica gel, in which a mixture of ethyl acetate and hexane is used as eluant. The title compound is obtained as foam.

Yield: 3.37 g (61.9% of theory)

Elementary analysis: $C_{20}H_{24}F_4N_2O_9S$ Cld: C 44.12 H 4.44 F 13.96 N 5.15 S 5.89 Fnd: C 44.30 H 4.49 F 14.00 N 5.20 S 5.94 f) 3-{N-[4-Fluoro-2-trifluoromethyl-3-benzoic acid-N-bis(2-hydroxyethyl)-amide]-sulfamoyl}-propionic acid 5.45 g (10 mmol) of the compound represented under Example 9e) is dissolved in 100 ml of ethanol. It is mixed with 25 ml (50 mmol) of 2N sodium hydroxide solution, heated briefly in a water bath and allowed to stir overnight at room temperature. The thin-layer chromatogram shows that only one product is produced. It is mixed with 40 ml (60 mmol) of ion exchanger H$^+$ (1.5 meg/ml), stirred for one-half hour more, suctioned off from the exchanger and the latter is rewashed well with water. The combined solutions are concentrated by evaporation in a vacuum, taken up in water and again concentrated by evaporation. The residue is then dissolved in distilled water and subjected to freeze-drying. The title compound is obtained as hygroscopic foam.

Yield: 3.78 g (84.6% of theory)

Elementary analysis: $C_{15}H_{18}F_4N_2O_7S$ Cld: C 40.36 H 4.06 F 17.02 N 6.28 S 7.18 Fnd: C 40.40 H 4.11 F 17.13 N 6.40 S 7.11

EXAMPLE 10

2-{2-(N-<4-Fluorophenyl-3,5-bis[acetic acid-N-(1-hydroxymethyl-2,3-dihydroxypropyl)-amide]>-sulfamoyl)acetylamino}-2-methyl-2-trifluoromethylacetic acid a) 2-{2-(N-<4-Fluorophenyl-3,5-bis[acetic acid-N-(6-hydroxy-2,2-dimethyl-1,3-dioxepan-5-yl)-amide]>-sulfamoyl)-acetic acid methyl ester 5.14 g (10 mmol) of the amino compound produced under Example 5e) is dissolved in 100 ml of dichloromethane. It is cooled off to −5° C., mixed with 0.791 g (10 mmol) of dry pyridine and then 1.726 g (10 mmol) of 2-chlorosulfonylacetic acid methyl ester in 10 ml of dichloromethane is instilled in it. It is stirred for 1 hour at the low temperature and then at room temperature overnight. It is then washed with water, dried on sodium sulfate and evaporated to dryness in a vacuum. The residue is purified by chromatography on silica gel. A mixture of ethyl acetate and ethanol is used as eluant. The title compound is obtained as amorphous foam.

Yield: 5.47 g (84.2% of theory)

Elementary analysis: $C_{27}H_{40}FN_3O_{12}S$ Cld: C 49.92 H 6.21 F 2.92 N 6.47 S 4.94 Fnd: C 49.98 H 6.27 F 2.96 N 6.51 S 4.90 b) 2-{2-(N-<4-Fluorophenyl-3,5-bis[acetic acid-N-(6-hydroxy-2,2-dimethyl-1,3-dioxepan-5-yl)-amide]>-sulfamoyl}-acetic acid 6.50 g (10 mmol) of the compound produced under Example 10a) is dissolved in 80 ml of ethanol. It is mixed with 10 ml (20 mmol) of 2N sodium hydroxide solution, heated briefly in a water bath and stirred overnight at room temperature. Then, it is evaporated to dryness in a vacuum, taken up in distilled water and mixed with 13.4 ml (20.1 mmol) of ion exchanger H$^+$ (1.5 meg/ml). It is stirred for 15 minutes at room temperature, filtered from the exchanger, rewashed well with distilled water and the title compound is obtained by freeze-drying.

Yield: 5.87 g (92.4% of theory)

Elementary analysis: $C_{26}H_{38}FN_3O_{12}S$ Cld: C 49.13 H 6.03 F 2.99 N 6.61 S 5.04 Fnd: C 49.08 H 6.11 F 3.06 N 6.72 S 5.10 c) 2-{2-(N-<4-Fluorophenyl-3,5-bis[acetic acid-N-(6-hydroxy-1,3-dioxepan-5-yl)-amide]>-sulfamoyl)-acetylamino}-2-methyl-2-trifluoromethyl-acetic acid 6.36 g (10 mmol) of the compound produced Under Example 10b) is dissolved in 100 ml of dichloromethane. It is cooled off to −5° C. and then 1.622 g (10 mmol) of carbonyldiimidazole is added to it, it is allowed to stir for 1 hour at the low temperature and then the solution of 1.571 g (10 mmol) of 2-trifluoromethyl-2-amino-propionic acid [represented according to H. Waternabe et al., Tetrahedron Letter 33, 4333 (1992)] as well as 1.012 g (10 mmol) of triethylamine in 20 ml of dichloromethane are added with stirring under further cooling. It is allowed to stir for 1 more hour at the low temperature, then for another 12 hours at room temperature. It is evaporated to dryness in a vacuum and the residue is purified by chromatography on silica gel. A mixture of ethyl acetate/ethanol/triethylamine is used as eluant. The title compound is eluted as triethylammonium salt. The free acid is obtained by treatment with 8 ml (12 mmol) of ion exchanger H$^+$ (1.5 meg/ml).

Yield: 5.28 g (68.1% of theory)

Elementary analysis: $C_{30}H_{42}F_4N_4O_{13}S$ Cld: C 46.51 H 5.46 F 9.81 N 7.23 S 4.14 Fnd: C 46.45 H 5.53 F 9.90 N 7.31 S 4.20 d) 2-{2-(N-<4-Fluorophenyl-3,5-bis[acetic acid-N-(1-hydroxymethyl-2,3-dihydroxypropyl)-amide]>-sulfamoyl)-acetylamino}-2-methyl-2-trifluoromethyl-acetic acid 3.874 g (5 mmol) of the acid produced under Example 10c) is dissolved in 80 ml of ethanol. It is mixed with 5 ml of ion exchanger H$^+$ and heated with stirring for 3 hours to 60° C. The thin-layer chromatogram shows that starting material is no longer present. It is filtered off from the exchanger, rewashed well with distilled water and evaporated to dryness in a vacuum. It is taken up again in distilled water and the title compound is obtained by freeze-drying. It is obtained as hygroscopic foam.

Yield: 3.26 g (93.8% of theory)

Elementary analysis: $C_{24}H_{34}F_4N_4O_{13}S$ Cld: C 41.50 H 4.93 F 10.94 N 8.07 S 4.62 Fnd: C 41.51 H 4.98 F 10.99 N 8.02 S 4.66

EXAMPLE 11

2-{2-(N-<4-Fluoro-2-trifluoromethylphenyl-3-acetic acid-N-(1-hydroxymethyl-2,3-dihydroxypropyl)-amide]-sulfamoyl>) -acetylamino}-acetic acid a) 2-{N-[4-Fluoro-2-trifluoromethylphenyl-3-acetic acid-N-(6-hydroxy-2,2-dimethyl-1,3-dioxepan-5-yl)-amide]-sulfamoyl}-acetylamino}-acetic acid-tert-butyl ester 5.59 g (10 mmol) of the compound produced under Example 1e) is suspended in 50 ml of ethanol. It is mixed with 15 ml (30 mmol) of 2N sodium hydroxide solution, heated briefly in a water bath and stirred overnight at room temperature. Then, it is evaporated to dryness in a vacuum. The residue is dissolved in distilled water, extracted with ether, and the solution is brought to pH 4 with ion exchanger H$^+$. It is filtered off from the exchanger, rewashed with distilled water and subjected to freeze-drying. The residue is dissolved in dry tetrahydrofuran, mixed with 1.31 g (10 mmol) of glycine-tert-butyl ester, 1.15 g (10 mmol) of hydroxysuccinimide and 2.27 g (11 mmol) of dicyclohexylcarbodiimide and stirred overnight at room temperature. It is suctioned off from the solid, concentrated by evaporation in a vacuum, taken up in ethyl acetate and washed with saturated sodium bicarbonate solution. After drying on sodium sulfate, it is evaporated to dryness in a vacuum and the residue is purified by chromatography on silica gel. A mixture of ethyl acetate and hexane is used as eluant. The title compound is obtained as foam.

Yield: 4.32 g (67.2% of theory)

Elementary analysis: $C_{24}H_{33}F_4N_3O_9S$ Cld: C 46.83 H 5.40 F 12.34 N 6.83 S 5.21 Fnd: C 46.90 H 5.45 F 12.39 N 6.78 S 5.16 b) 2-{2-(N-<4-Fluoro-2-trifluoromethylphenyl-3-acetic acid-N-(1-hydroxymethyl-2,3-dihydroxypropyl)-amide]-sulfamoyl>-acetylamino}-acetic acid 6.16 g (10 mmol) of the compound produced under Example 1g) is dissolved in 100 ml of moist ethanol. 5 ml of ion exchanger H⁺ is added to it and heated with stirring to 60°–70° C. After 90 minutes, starting material can no longer be detected. It is suctioned off from the exchanger, rewashed well with water and concentrated by evaporation in a vacuum to a viscous oil. It is taken up in distilled water and the title compound is obtained by freeze-drying as hygroscopic foam. Yield: 4.79 g (92.3% of theory) Elementary analysis: $C_{17}H_{21}F_4N_3O_9S$ Cld: C 39.31 H 4.07 F 14.63 N 8.09 S 6.17 Fnd: C 39.40 H 4.14 F 14.55 N 8.17 S 6.26

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A disubstituted p-fluorobenzene sulfonamide of the formula I

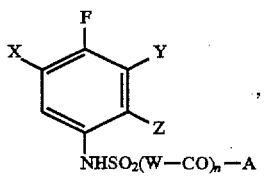

in which

Z stands for a $CF_3$ group or a hydrogen atom,

Y stands for a $(CH_2)_o CONR^1R^2$ group with o meaning 1 and $R^1$ and $R^2$, independently of one another, meaning hydrogen or a $C_1$–$C_6$ alkyl group optionally substituted by 1 to 4 hydroxy groups, X stands for a hydrogen atom or for one of the meanings indicated for Y, W stands for a $C_0$–$C_6$ alkylene group, optionally substituted by 1 to 4 hydroxy groups or interrupted by 1 to 2 oxygen atoms, where $C_0$ is a direct bond, n stands for numbers 0 or 1, A stands for radicals —OH, $OR^3$, —$CF_3$, —$CH_2CF_3$, —NH—$CR^3(CF_3)$—COOH or —$NHCH_2COOH$ with $R^3$ meaning a hydrogen atom or a straight-chain or branched-chain $C_1$–$C_6$ alkyl group optionally substituted by 1 to 2 hydroxy group(s), provided that X stands for a hydrogen atom if Z means a $CF_3$ group, that X has one of the meanings indicated for Y, if Z stands for a hydrogen atom, that A is $CF_3$, or —NH—$CR^3(CF_3)$—COOH when Z is hydrogen, and that optionally the acid groups present in the molecule are present in the form of their amides or in the form of salts with organic or inorganic bases.

2. A compound according to claim 1, wherein Z stands for a hydrogen atom and X has the same meaning as Y.

3. A compound according to claim 1, wherein Y stands for

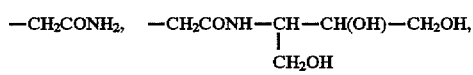

—$CH_2CONHCH(CH_2OH)_2$,

—$CH_2CONH$—$CH_2$—$CH(OH)$—$CH_2OH$, or

—$CH_2CONH$—$CH_2(CH)_4$—$CH_2OH$.
            |
           OH

4. A compound according to claim 1, wherein W stands for

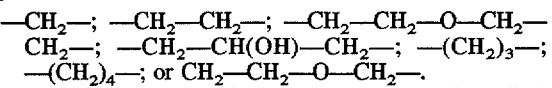

5. A compound according to claim 1, wherein radical —(W—CO)$_n$—A stands for

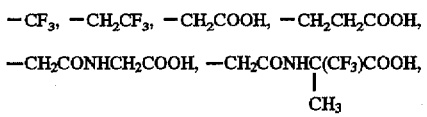

or —$CH_2CONHCH(CF_3)COOH$.

6. A compound of claim 1, with a pK of from 2 to 9.

7. A compound of claim 1, with a pK of from 6 to 8.

8. A compound according to claim 1 which is:

2-{N-[4-Fluoro-2-trifluoromethylphenyl-3-acetic acid-N-(1-hydroxymethyl-2,3-dihydroxypropyl)-amide]-sulfamoyl}-acetic acid;

3-{N-[4-fluoro-2-trifluoromethylphenyl-3-acetic acid-N-(1-hydroxy-2,3-dihydroxypropyl)-amide]-sulfamoyl}-propionic acid;

3-{N-[4-fluoro-2-trifluoromethylphenyl-3-carbamoylmethyl]-sulfamoyl}-propionic acid;

N-{4-fluorophenyl-3,5-bis[acetic acid-N-(1-hydroxymethyl-2,3-dihydroxypropyl)-amide]}-trifluoromethylsulfonamide;

N-{4-fluorophenyl-3,5-bis[acetic acid-N-(1-hydroxymethyl-2,3-dihydroxypropyl)-amide]}-2,2,2-trifluoroethylsulfonamide;

2-{2-(N-4-fluorophenyl-3,5-bis-acetic acid-N-(1-hydroxymethyl-2,3-dihydroxypropyl)-amide-]-sulfamoyl)-acetylamino)}-2-methyl-2-trifluoromethyl-acetic acid; or 2-{2-N-4-fluoro-2-trifluoromethylphenyl-3-[acetic acid-N-(1-hydroxymethyl-2,3-dihydroxypropyl)-amide-]-sulfamoyl-acetylamino)}-acetic acid.

9. A diagnostic agent containing at least one compound of formula I of claim 1 and at least one additive usual in galenicals.

10. An NMR diagnostic method which comprises administering a compound of the formula I of claim 1 as an NMR diagnostic agent.

11. A method for in vivo pH measurement which comprises administering a compound of the formula I of claim 1 and conducting NMR spectroscopic measurement of the change in chemical shift of the $^{19}F$ signal relative to a reference signal to determine pH.

12. A process for the production of a disubstituted p-fluorobenzenesulfonamide of formula I

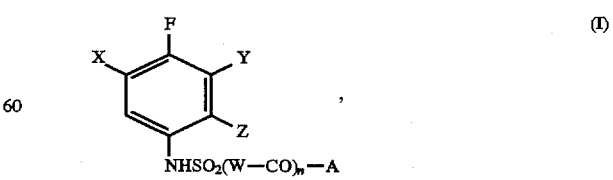

in which

Z stands for a $CF_3$ group or a hydrogen atom,

Y stands for a $(CH_2)_o CONR^1R^2$ group with o meaning 1 and $R^1$ and $R^2$, independently of one another, meaning hydrogen or a $C_6$–$C_6$ alkyl group optionally substituted by 1 to 4 hydroxy groups, X stands for a hydrogen atom or for one of the meanings indicated for Y, W stands for a $C_0$–$C_6$ alkylene group, optionally substituted by 1 to 4 hydroxy groups or interrupted by 1 to 2 oxygen atoms, where $C_0$ is a direct bond, n stands for numbers 0 or 1, A stands for radicals —OH, $OR^3$, —$CF_3$, —NH—$CR^3$ ($CF_3$)—COOH or —$NHCH_2$ COOH with $R^3$ meaning a hydrogen atom or a straight-chain or branched-chain $C_1$–$C_6$ alkyl group optionally substituted by 1 to 2 hydroxy group(s), provided that X stands for a hydrogen atom if Z means a $CF_3$ group, that X has one of the meanings indicated for Y, if Z stands for a hydrogen atom, that A is $CF_3$, or —NH—$CR^3$ ($CF_3$)—COOH when Z is hydrogen, and that optionally the acid groups present in the molecule are present in the form of their amides or in the form of salts with organic or inorganic bases, which comprises reacting a compound of formula II

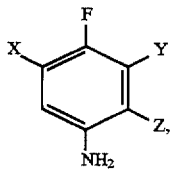
(II)

in which

Y and X have the above-indicated meaning, and the hydroxy and carbonyl groups optionally contained in them optionally are present in protected form, with a compound of formula III $$ClSO_2(W—CO)_n—A \qquad (III),$$

in which

W, n and A have the above-indicated meaning, and the hydroxy and carboxy groups optionally contained in A optionally are present in protected form, removing the optionally present protective groups, and if desired, converting the acid groups optionally present in the molecule with organic or inorganic bases to the corresponding salts or, optionally after activation of the acid groups, by reaction with an amine to the corresponding amides.

13. A process for the production of a diagnostic agent according to claim 9 which comprises suspending or dissolving the p-fluorobenzenesulfonamide in an aqueous medium such that it is in a form suitable for enteral or parenteral administration.

\* \* \* \* \*